United States Patent [19]

Winston et al.

[11] Patent Number: 5,432,147
[45] Date of Patent: Jul. 11, 1995

[54] METHOD OF CONTROLLING FUNGAL DISEASE IN CULTIVATED PLANTS

[75] Inventors: Anthony E. Winston, East Brunswick; Alfredo Vinci, Dayton, both of N.J.

[73] Assignee: Church & Dwight Co., Inc., Princeton, N.J.

[21] Appl. No.: 325,472

[22] Filed: Oct. 19, 1994

Related U.S. Application Data

[62] Division of Ser. No. 269,154, Jun. 30, 1994, Pat. No. 5,389,386.

[51] Int. Cl.⁶ .................... C05G 3/02; A01N 59/00; A01N 31/02; A01N 31/14
[52] U.S. Cl. .................... 504/101; 424/715; 424/716; 424/717; 514/717; 514/718; 514/723; 514/724; 514/730; 514/731; 514/777; 514/782
[58] Field of Search .................... 424/715, 716, 717; 514/717, 718, 723, 724, 730, 731, 777, 782; 504/101

[56] References Cited

U.S. PATENT DOCUMENTS

| | | | |
|---|---|---|---|
| 3,236,626 | 2/1966 | Lindner | 504/101 |
| 3,984,570 | 10/1976 | Bent et al. | 514/723 |
| 4,599,233 | 7/1986 | Misato et al. | 424/717 |
| 4,876,102 | 10/1989 | Feeney et al. | 426/550 |
| 5,026,734 | 6/1991 | Browning | 514/723 |
| 5,185,153 | 2/1993 | Pollock et al. | 424/440 |
| 5,270,032 | 12/1993 | Pollock et al. | 424/49 |
| 5,286,492 | 2/1994 | Dettmar et al. | 424/458 |
| 5,330,964 | 7/1994 | Alesi, Jr. | 424/717 |
| 5,338,551 | 8/1994 | LaJoie | 424/717 |
| 5,342,630 | 8/1994 | Jones | 424/717 |
| 5,346,704 | 9/1994 | LaJoie | 424/717 |

FOREIGN PATENT DOCUMENTS

| | | |
|---|---|---|
| 4714891 | 5/1972 | Japan. |
| 5396319 | 8/1978 | Japan. |

OTHER PUBLICATIONS

Chemical Abstracts 95:163726s (1981).

*Primary Examiner*—Allen J. Robinson
*Assistant Examiner*—John D. Pak
*Attorney, Agent, or Firm*—Charles B. Barris

[57] ABSTRACT

The present invention provides a method for controlling fungal disease in cultivated crops. The aqueous fungicide formulation which is applied to pre-harvest and post-harvest crops contains ingredients which are biocompatible for purposes of agricultural and horticultural applications. Illustrative of a formulation which is harmless to animals and humans is an aqueous solution having a content of potassium bicarbonate, potassium carbonate, nonionic surfactant and xanthan gum. The combination of nonionic surfactant and xanthan gum functions as an effective spreader-sticker medium for forming a film-like coating on plant surfaces. The adherent coating exhibits both immediate and long duration fungicidal activities.

2 Claims, No Drawings

METHOD OF CONTROLLING FUNGAL DISEASE IN CULTIVATED PLANTS

This application is a division of application Ser. No. 08/269,154, filed Jun. 30, 1994 now U.S. Pat. No. 5,389,386.

BACKGROUND OF THE INVENTION

The control of phytopathogenic fungi is of great economic importance since fungal growth on plants or on parts of plants inhibits production of foliage, fruit or seed, and the overall quality of a cultivated crop. About 25 percent of all fungal diseases in agriculture and horticulture is caused by powdery mildew phytopathogens.

Because of the vast economic ramifications of fungal propagation in agricultural and horticultural cultivations, a broad spectrum of fungicidal and fungistatic products have been developed for general and specific applications.

Of particular interest with respect to the present invention embodiments are fungicide compositions which contain an inorganic bicarbonate or carbonate compound. It is known that bicarbonate and carbonate compounds exhibit fungicidal properties for agricultural purposes.

Phytopathology, 48, 169 (1931) by R. Ho Marloth describes studies involving the physiology of fungi. The reference reports studies which demonstrate that sodium and potassium bicarbonate and carbonate salts are toxic to fungi such as *Penicillum italicum* and *Penicillum digitalum*.

U.S. Pat. No. 1,560,558 discloses the use of salts such as lithium carbonate, sodium carbonate, sodium bicarbonate, potassium bicarbonate, potassium carbonate and ammonium bicarbonate as fungicide ingredients.

U.S. Pat. No. 4,599,233 describes a fungicide composition which consists of sodium bicarbonate in combination with a surface active food emulsifier such as sorbitan monostearate.

Japanese patent 53118523 describes the combination of sodium bicarbonate and lecithin as an active agent for the control of agricultural and fruit storage fungus diseases.

Japanese patent 56043207 describes a biocidal composition containing sodium bicarbonate and a polyglycerol fatty acid ester. The biocide controls *Penicillum digitatum* on oranges, *Sphaerotheca fuligenea* on cucumbers, *Piricularia oryzae* on rice, and mosaic virus on tomatoes.

Japanese patent 60097909 describes a soil fungicide prepared by admixing slaked lime with sodium bicarbonate, potassium bicarbonate, boric acid and phenolphthalein.

German patent DE 2927994 describes a fungicide which consists of sodium bicarbonate incorporated into a food-compatible surfactant such as saccharose laurate.

Japanese patent 57062208 describes horticultural fungicides in which the addition of sodium bicarbonate to polyoxin or thiophanatemethyl increases the fungicidal activity of the organic biocide against *Botrytis cinerea* on cucumbers.

Japanese patent 58023609 describes an agricultural fungicide composed of a mixture of sodium bicarbonate or potassium bicarbonate with cupric hydroxide, basic copper carbonate or basic copper sulfate. The combination of ingredients exhibits a synergistic fungicidal effect against cucumber early blight, tomato wilt, rice sheath blight, rice blast and citrus canker.

There remains a continuing need for improved methods for providing preventive and curative fungicidal activity for the protection of cultivated plants with a minimum of phytotoxic side effects, and with safety for animals and humans.

Accordingly, it is an object of this invention to provide a method of controlling fungal disease in cultivated plants.

It is another object of this invention to provide a method for controlling fungal disease such as mildew in agricultural and horticultural plants with an aqueous fungicidal formulation having a content of bicarbonate salt and other ingredients which are harmless to animals and humans.

It is another object of this invention to provide a method of controlling powdery mildew and downy mildew in pre-harvest and post-harvest crops with an aqueous formulation which forms a coating on plant matter exhibiting fungicidal activity of sustained duration.

Other objects and advantages of the present invention shall become apparent from the accompanying description and examples.

DESCRIPTION OF THE INVENTION

One or more objects of the present invention are accomplished by the provision of a method for controlling fungal disease in cultivated plants which comprises contacting the plant matter with a fungicidally effective application of an aqueous formulation which has a content comprising (1) about 0.1–3 weight percent of an ingredient selected from alkali metal and ammonium bicarbonates; and (2) about 0.01–0.5 weight percent of an ingredient selected from nonionic alkoxylated alkanol and alkoxylated alkylphenol surfactants having an HLB between about 8–15; based on the formulation weight.

In another embodiment this invention provides a method for controlling fungal disease in cultivated plants which comprises contacting the plant matter with a fungicidally effective application of an aqueous formulation which has a content comprising (1) about 0.1–3 weight percent of an ingredient selected from alkali metal and ammonium bicarbonates; (2) about 0.01–0.5 weight percent of an ingredient selected from nonionic alkoxylated alkanol and alkoxylated alkylphenol surfactants having an HLB between about 8–15; and (3) about 0.01–0.4 weight percent of a water-soluble polymeric thickener-film forming ingredient; based on the formulation weight.

In another embodiment this invention provides a method for controlling fungal disease in cultivated plants which comprises contacting the plant matter with a fungicidally effective application of an aqueous formulation which has a content comprising (1) about 0.1–3 weight percent of an ingredient selected from alkali metal and ammonium bicarbonates; (2) about 0.01–0.5 weight percent of an ingredient selected from nonionic alkoxylated alkanol and alkoxylated alkylphenol surfactants having an HLB between about 8–15; and (3) about 0.1–2 weight percent of an ingredient selected from phosphorus-containing fertilizer compounds; based on the formulation weight; wherein the ingredients have a formulated fertilizer ratio of nitrogen, phosphorus and potassium elements.

In a further embodiment this invention provides a method for controlling fungal disease in cultivated plants which comprises contacting the plant matter with a fungicidally effective application of an aqueous formulation which has a content comprising (1) about 0.1–3 weight percent of an ingredient selected from alkali metal and ammonium bicarbonates; (2) about 0.01–0.5 weight percent of an ingredient selected from nonionic alkoxylated alkanol and alkoxylated alkylphenol surfactants having an HLB between about 8–15; (3) about 0.01–0.4 weight percent of a water-soluble polymeric thickener-film forming ingredient; and (4) about 0.1–2 weight percent of an ingredient selected from phosphorus-containing fertilizer compounds; based on the formulation weight; wherein the ingredients have a formulated fertilizer ratio of nitrogen, phosphorus and potassium elements.

An invention aqueous formulation can be prepared by pre-blending the solid ingredients, and then dispersing the blended admixture in an aqueous medium to a selected concentration of bicarbonate ingredient.

An invention aqueous formulation can be prepared as a concentrated medium which is diluted further before usage, or the dilute aqueous formulation can be prepared directly by adding the individual ingredients of a pre-blend of ingredients to an aqueous medium.

An invention dilute aqueous fungicidal solution is in a ready-to-use form which can be applied directly to the foliage of plants, bushes and trees, such as by electrodynamic spraying techniques. A dry coating forms on the plant matter surfaces after the aqueous medium has evaporated, and typically is in the form of a film-like coating when an applied formulation contains a polymeric thickener-film forming ingredient.

The bicarbonate salt ingredient of an invention fungicide formulation is sodium bicarbonate, potassium bicarbonate or ammonium bicarbonate, or any mixture thereof.

Illustrative of a bicarbonate salt ingredient in a formulation are sodium, potassium or ammonium bicarbonate; or mixtures such as sodium bicarbonate and potassium bicarbonate; sodium bicarbonate and ammonium bicarbonate; potassium bicarbonate and ammonium bicarbonate; sodium bicarbonate, potassium bicarbonate and ammonium bicarbonate; and the like.

The bicarbonate salt ingredient can be partially substituted with between about 0.5–20 weight percent of a basic ingredient selected from alkali metal and ammonium carbonates. Suitable carbonates include sodium carbonate, potassium carbonate, ammonium carbonate or lithium carbonate, or any mixture thereof.

Multiple inorganic salt compounds can be utilized in a broad range of molar quantities relative to each other. In one aspect the molar quantity of an optional carbonate salt compound is determined by pH control considerations when aqueous formulations are prepared. The content of a carbonate salt compound can be varied to control the pH of an aqueous fungicide formulation at a desired level in the range of about 7.5–11. An aqueous fungicide formulation of the present invention tends to have a higher fungicidal activity at higher pH values.

An invention aqueous formulation is in the form of a stable aqueous dispersion which exhibits excellent spreader-sticker and film-forming properties when applied to plant foliage. A critical aspect of the spreader-sticker and film-forming properties is the utilization of a narrowly specific type of nonionic surfactant ingredient which provides suitable dispersant properties.

The surfactant ingredient of an invention aqueous fungicide formulation is selected from nonionic alkoxylated alkanol and alkoxylated alkylphenol surface active derivatives which have an HLB (hydrophile-lipophile balance) between about 8–15. A preferred HLB range is between about 8–11.

Illustrative of nonionic surfactants are $C_8$–$C_{18}$ alcohols with 1–15 moles of ethylene oxide per mole of alcohol, $C_6$–$C_{18}$ alcohols with 1–10 moles of propylene oxide per mole of alcohol, $C_6$–$C_{18}$ alcohols with 1–15 moles of ethylene oxide and 1–10 moles of propylene oxide per mole of alcohol, $C_6$–$C_{18}$ alkylphenols with 1–15 moles of ethylene oxide and/or propylene oxide, and mixtures of these surfactants.

A preferred class of nonionic surfactants are those selected from $C_9$–$C_{15}$ alcohols condensed with 2–15 moles of ethylene oxide. Illustrative of these surfactants are those available under the trademark Neodol (Shell Chemical Company), such as Neodol 1-9, Neodol 23–6.5, Neodol 25–3, Neodol 25–9, Neodol 25–12, Neodol 45–13, Neodol 91–2.5, Neodol 91–8, and the like.

The optional thickener-film forming ingredient of an invention fungicide formulation is selected from water-soluble organic polymers which exhibit pseudoplastic rheological properties in an aqueous medium.

The term "water-soluble" as employed herein refers to a thickener ingredient which has a solubility of at least about one gram per 100 grams of water at 25° C.

The term "pseudoplastic" as employed herein refers to the rheological behavior of an aqueous solution containing a dissolved thickener ingredient, in which the apparent viscosity of the aqueous solution decreases with increasing shear rate.

Illustrative of water-soluble polymers which exhibit pseudoplastic properties in an aqueous medium are gum arabic, gum karaya, gum tragacanth, guar gum, locust bean gum, xanthan gum, carrageenan, alginate salt, casein, dextran, pectin, agar, 2-hydroxyethyl starch, 2-aminoethyl starch, 2-hydroxyethyl cellulose, methyl cellulose, carboxymethyl cellulose salt, cellulose sulfate salt, polyacrylamide, methyl vinyl ether/mateic acid copolymer alkali metal salt, styrene/maleic acid copolymer alkali metal salt, ethylene/maleic acid copolymer alkali metal salt, poly(meth)acrylate alkali metal salt, and the like.

Many of the water-soluble polymers are large volume commercial products. Sodium carboxymethyl cellulose (CMC) is available in powder or granular form having a particle size of 50–200 microns. CMC is available in a degree of substitution (DS) range of 0.38–1.4.

One type of preferred aqueous formulation in accordance with the present invention is one containing alkali metal or ammonium bicarbonate, alkali metal or ammonium carbonate, a $C_{10}$–$C_{15}$ oxyethylated alcohol ether surfactant, and a hydrocolloid gum.

The ingredients in an invention fungicide formulation can be selected to include nitrogen, phosphorus and potassium elements in a ratio that qualifies the composition to function as a fertilizer in addition to its function as a fungicide, when applied to cultivated crops, such as a NPK ratio of 5-10-5. When an aqueous solution containing fertilizer elements is sprayed on plant foliage, there is direct absorption of the fertilizer elements into the leaves.

Besides nitrogen, phosphorus and potassium, an invention fungicide fertilizer composition can contain trace elements, and other essential elements as exemplified by sulfur as contained in a compound such as sodium bisulfite or thiourea.

An invention fungicide formulation can include one or more other biologically active ingredients, such as those which exhibit herbicidal, insecticidal or plant growth regulating activity.

A fungicide formulation of the present invention has a novel combination of properties for the practice of pesticide control in agricultural and horticultural applications.

The bicarbonate ingredient and the optional carbonate ingredient exhibit fungicidal properties, and the efficacy of any additionally included organic pesticide ingredient usually is enhanced by the presence of the combination of bicarbonate and/or carbonate salts. A lesser quantity of optional pesticide ingredient can be employed to achieve a desired degree of pest control.

A present invention aqueous fungicide medium can be formulated to exhibit no phytotoxicity, or to minimize the toxic effects of salt stress on plants by the bicarbonate and carbonate ingredients.

All of the fungicide formulation ingredients are biocompatible when the composition is applied in an agricultural environment. The bicarbonate, carbonate, surfactant and thickener-film forming ingredients are all harmless to animals and humans.

A significant feature of a present invention fungicide formulation is the presence of the selected types of surfactant and thickener-film forming ingredients, which function as a spreader-sticker medium when the fungicide formulation is applied to plant foliage as an aqueous solution. An applied aqueous solution forms an adherent coating of ingredients on plant foliage or fruit. The surfactant ingredient aids in spreading and sticking the fungicide formulation ingredients to the foliage or fruit to which it is applied. The thickener-film forming ingredient increases the amount of aqueous fungicide composition which adheres to the plant matter surfaces because of its static high apparent viscosity. During a spraying procedure, the thickener-film forming ingredient contributes a low mobile viscosity to the spray solution, which facilitates the spraying action. After spraying, the resultant film-like coating resists drifting under wind conditions, and exhibits humectant properties in addition to enhanced fungicidal activity.

A present invention fungicide formulation preferably is employed in a diluted form which provides a bicarbonate ingredient concentration between about 0.25–0.75 weight percent, and a surfactant ingredient concentration between about 0.025–0.05 weight percent, based on the aqueous formulation weight.

Another important advantage of an invention fungicide formulation derives from the water-solubility of the contained ingredients. The solid coating of an invention fungicide formulation on plant matter surfaces can be removed readily by water-washing. Conventional fungicide formulations which contain a petroleum-based spreader-sticker ingredient leave an oily residue on treated plant foliage or fruit which is difficult to remove.

A present invention aqueous fungicide formulation is adapted for application to harvested crops to prevent or eradicate fungal disease, or to inhibit re-infection by phytopathogenic fungi.

A present invention fungicide formulation is qualified to combat a broad range of phytopathogenic fungi. Illustrative of fungi which are susceptible to the fungicidal activity of a present invention fungicide formulation include *Venturia inaequalis* which causes apple scab; *Sclerotinia sclerotiorum* which causes vegetable rot; *Botrytis cinerea* which causes blossom and fruit rot of ornamentals, fruits and vegetables; *Pericularia oryzae* which causes rice blast; *Puccinia recondita* which causes leaf rusts of wheat, oats and grasses; *Aspergillus niger* which causes cotton boll rot; *Aspergillus flavus* which causes mold growth on peanuts; and *Aspergillus terrus* which is common in soil and infects root systems.

A present invention fungicide formulation has particular advantage for the control of powdery mildew and downy mildew in crops such as ornamental stock, bedding plants, turf, cereals, vegetables, fruits, forest trees, and the like.

Illustrative of particular crops are pre-harvest and post-harvest stages of grape, apple, pear, peaches, strawberry, raspberry, cucumber, rose, and the like.

A present invention fungicide formulation is biocidally effective against powdery mildew species which include *Erysiphe asperifolium, Erysiphe betae, Erysiphe cichoracearum, Erysiphe cruciferarum, Erysiphe galeopsidis, Erysiphe graminis, Erysiphe pisi, Erysiphe polygoni, Erysiphe ranunculi, Erysiphe trifolii, Erysiphe verbasci, Microsphaera alphitoides, Oidium euonymi-japonicae, Oidium hortensiae, Podosphaera leucotricha, Podosphaera tridactyla, Sphaerotheca alchemillae, Sphaerotheca fuliginea, Sphaerotheca maculans, Sphaerotheca pannosa, Uncinula bicornis* and *Uncinula necator.*

A present invention fungicide formulation also is biocidally effective against downy mildew species which include *Peronospora antirrhini, Peronospora arborescens, Peronospora destructor, Peronospora farinosa, Peronospora ficariae, Peronospora galligena, Peronospora grisea, Peronospora lamii, Peronospora parasitica, Peronospora sparsa, Peronospora trifoliorum, Peronospora viciae, Pseudoperonospora humuli,* and *Plasmopara vitacola.*

The following examples are further illustrative of the present invention. The components and specific ingredients are presented as being typical, and various modifications can be derived in view of the foregoing disclosure within the scope of the invention.

EXAMPLE I

This Example illustrates the comparative spreader-sticker properties of liquid nonionic surfactants in aqueous alkali metal bicarbonate fungicide formulations.

The data in Table A and Table B for nonionic surfactants is provided in accordance with the following procedures.

The "salting out" rating of a nonionic surfactant is determined by dissolving the surfactant (10 g) in water (150 g), and adding sodium or potassium bicarbonate (40 g). The degree of salting out of the surfactant as a separate phase from the aqueous solution is rated qualitatively by observation.

The "wetting" rating is determined with coated microscopic slides resembling a waxy leaf surface. The slides are prepared by dipping in a 0.1% w/w solution of lanolin in petroleum ether, and dried.

An aqueous stock solution is prepared which contains 20% of sodium or potassium bicarbonate and 5% of nonionic surfactant. The stock solution is diluted with water to 0.5% sodium or potassium bicarbonate and 0.125% nonionic surfactant. The coated slides are dipped in the diluted stock solution, and the degree of slide wetting is observed.

After a dipped slide is dried, the coating on the slide surface is viewed with a Leitz light microscope equipped with a Sony monitor and color video printer. Photographs are taken at 25x and 100x magnification, and the photographs are examined for crystal uniformity, size and surface coverage.

TABLE A

Potassium Bicarbonate/Nonionic Surfactant
Aqueous Formulation Properties

| No. | Surfactant(a) | Surfactant HLB | Salting Out Rating | Wetting Rating | Microscope Rating |
|---|---|---|---|---|---|
| 1 | Neodol 91-8 | 13.9 | A | B | A |
| 2 | Neodol 1-9 | 13.9 | A | A | A |
| 3 | Neodol 25-9 | 13.1 | B | A | A |
| 4 | Neodol 25-12 | 14.4 | A | B | B |
| 5 | Neodol 45-13 | 14.5 | A | A | C |
| 6 | Triton X-102 | 14.6 | A | B | D |
| 7 | Neodol 1-7 | 12.9 | C | A | D |
| 8 | Neodol 25-7 | 12.3 | E | B | D |
| 9 | Neodol 91-6 | 12.5 | C | C | D |
| 10 | Triton X-305 | 17.3 | A | D | D |
| 11 | Triton X-705 | 18.5 | A | C | D |

Salting Out Rating: A (best) → E (worst)
Wetting Rating: A = excellent, B = good, C = average, D = fail
Microscope Rating: A = excellent, B = good, C = average, D = fail
(a)
1. $C_9$–$C_{11}$ alcohol ether with average of 8 moles of ethylene oxide (Shell).
2. $C_{11}$ alcohol ether with average of 9 moles of ethylene oxide (Shell).
3. $C_{12}$–$C_{15}$ alcohol ether with average of 9 moles of ethylene oxide (Shell).
4. $C_{13}$–$C_{15}$ alcohol ether with average of 12 moles of ethylene oxide (Shell).
5. $C_{14}$–$C_{15}$ alcohol with average of 13 moles of ethylene oxide (Shell).
6. n-octylphenol ether with an average of 13 moles of ethylene oxide (Rohm & Haas).
7. $C_{11}$ alcohol ether with an average of 7 moles of ethylene oxide (Shell).
8. $C_{12}$–$C_{15}$ alcohol ether with an average of 7 moles of ethylene oxide (Shell).
9. $C_9$–$C_{11}$ alcohol ether with an average of 6 moles of ethylene oxide (Shell).
10. n-octylphenol ether with an average of 30 moles of ethylene oxide (Rohm & Haas).
11. n-octylphenol ether with an average of 70 moles of ethylene oxide (Rohm & Haas).

TABLE B

Potassium Bicarbonate/Nonionic Surfactant
Aqueous Formulation Properties

| No. | Surfactant(a) | Surfactant HLB | Salting Out Rating | Wetting Rating | Microscope Rating |
|---|---|---|---|---|---|
| 1 | Neodol 25-9 | 13.1 | A | A | A |
| 2 | Renex 30 | 14.5 | A | A | A |
| 3 | Atplus S-10 | 14.5 | B | A | A |
| 4 | Neodol 25-12 | 14.4 | A | A | B |
| 5 | Neodol 91-8 | 13.9 | A | B | B |
| 6 | Neodol 1-9 | 13.9 | A | A | B |
| 7 | Neodol 45-13 | 14.5 | A | B | B |
| 8 | Glucopon 225CS | NA | A | B | D |
| 9 | Triton BG-10 | 14.8 | A | B | D |
| 10 | Ethomeen T/25 | NA | A | B | D |
| 11 | Triton X-102 | 14.6 | A | B | D |
| 12 | Glycosperse 0-20 | 15.0 | A | C | D |
| 13 | Triton X-305 | 17.3 | A | C | D |
| 14 | Centrolex F | 12.0 | B | D | D |
| 15 | Glycosperse L-20 | 17.0 | A | C | D |
| 16 | Polytergent CS-1 | NA | A | C | D |
| 17 | Triton X-705 | 18.5 | A | C | D |

Salting Out Rating: A (best) → E (worst)
Wetting Rating: A = excellent, B = good, C = average, D = fail
(a)
Microscope Rating: A = excellent, B = good, C = average, D = fail
2. tridecyl alcohol ether with average of 12 moles of ethylene oxide (ICI Americas).
3. urea complex of polyoxylated tridecyl ether (ICI Americas).
8. alkylmono and oligoglucopyranoside (Henkel).
9. alkylaryl polyether alcohols (Union Carbide).
10. hydrogenated tallow amine with average of 15 moles of ethylene oxide (Akzo).
12. sorbitol mono-oleate with average of 20 moles of ethylene oxide (Lonza).
14. soy lecithin (Central Soya).
15. sorbitol monolaurate with average of 20 moles of ethylene oxide (Lonza).
16. ethoxylated alkanol succinate (Olin).

EXAMPLE II

This Example illustrates the effectiveness of present invention fungicide formulations in comparison with prior art formulations for control of fungal disease in cultivated plants.

Leaflets, heavily infected with *Sphaerotheca pennosa var rosae* powdery mildew, are detached from greenhouse-grown Mary Devor cultivar roses. The stem end of the leaflet is placed in an open aluminum pan containing 2% water agar. The leaflets are then sprayed to run off with a solution of the test formulation. After 18–24 hours the quantity of powdery mildew remaining is scored as follows:

0 = no mildew, 1 = 10% coverage, 2 = 30% coverage, 3 = 50% coverage, 4 = 70% coverage, 5 = 90+% coverage.

Each test formulation is evaluated twice using 10 replicates each test. Statistical analyses are performed by combining the two tests to provide 20 replications per formulation.

The following formulations are evaluated:

| | Controls | | Examples | | | |
|---|---|---|---|---|---|---|
| | A | B | 1 | 2 | 3 | 4 |
| Neodol 25-12[1] | 0 | 0 | 5 | 0 | 0 | 0 |
| Neodol 1-9[2] | 0 | 0 | 0 | 5 | 0 | 0 |
| Neodol 23-5[3] | 0 | 0 | 0 | 0 | 5 | 0 |
| Polytergent SL62[4] | 0 | 0 | 0 | 0 | 0 | 5 |
| Tween 40[5] | 5 | 0 | 0 | 0 | 0 | 0 |
| Tween 20[6] | 0 | 5 | 0 | 0 | 0 | 0 |
| $KHCO_3$ | 20 | 20 | 20 | 20 | 20 | 20 |
| Water | 75 | 75 | 75 | 75 | 75 | 75 |

[1] Neodol 25-12 is a linear ethoxylated alcohol (Shell) with 12–15 carbons in the alkyl chain, an average of 12 moles of ethylene oxide, and an HLB of 14.4.
[2] Neodol 1-9 is a linear ethoxylated alcohol (Shell) with 10–12 carbons in the alkyl chain, an average of 9 moles of ethylene oxide, and an HLB of 13.9.
[3] Neodol 23-5 is a linear ethoxylated alcohol (Shell) with 12–13 carbons in the alkyl chain, an average of 5 moles of ethylene oxide, and an HLB of 10.7.
[4] Polytergent SL62 is a proprietary ethoxylated/propoxylated alcohol with an HLB of 14.0 (Olin).
[5] Tween 40 is sorbitan monopalmitate ethoxylated with 4 moles of ethylene oxide, and has an HLB of 15.6 (ICI Americas).
[6] Tween 20 is sorbitan monolaurate ethoxylated with 20 moles of ethylene oxide, and has an HLB of 16.6 (ICI Americas).

The above solutions are diluted to 2.5% by volume for application to the leaflets being treated, and the results are as follows:

| | Mean score | Std dev. | Sig.* |
|---|---|---|---|
| Water Control | 5.0 | 0.00 | a |
| $KHCO_3$ Control | 3.6 | 0.60 | b |
| Control A | 3.4 | 0.99 | b |
| Control B | 2.65 | 0.81 | c |
| Example 1 | 1.0 | 0.65 | d,e |
| Example 2 | 0.85 | 0.59 | d |
| Example 3 | 1.65 | 0.93 | f |

|           | Mean score | Std dev. | Sig.* |
|-----------|------------|----------|-------|
| Example 4 | 1.45       | 0.89     | e,f   |

*Products with different letters are significantly different (p, 0.05) based on Duncan's multiple range test.

The comparative data demonstrate that surfactants of the invention formulations promote the fungicidal activity of bicarbonates more effectively than surfactants disclosed in prior art such as U.S. Pat. No. 4,599,233 by Misato et al.

The following comparative data illustrate that even when HLB of surfactants are in the same range, ethoxylated surfactants of the present invention formulations are more effective for fungal control than food grade emulsifiers of the prior art.

|                     | Controls |      |      | Examples |      |      |
|---------------------|----------|------|------|----------|------|------|
|                     | C        | D    | E    | 5        | 6    | 7    |
| Tween 85[2]         | 5.0      | 1.0  | 1.0  | 0.0      | 0.0  | 0.0  |
| Neodol 1-5[1]       | 0.0      | 0.0  | 0.0  | 5.0      | 1.0  | 1.0  |
| $KHCO_3$            | 20.0     | 20.0 | 0.0  | 20.0     | 20.0 | 0.0  |
| $NaHCO_3$           | 0.0      | 0.0  | 10.0 | 0.0      | 0.0  | 10.0 |
| Water               | 75.0     | 79.0 | 89.0 | 75.0     | 79.0 | 89.0 |

[1]Neodol 1-5 is a 5 mole ethoxylated $C_{10}$-$C_{11}$ alcohol with an HLB of 11.2 (Shell).
[2]Tween 85 is a 20 mole ethoxylate of sorbitan trioleate with an HLB of 11.0 (ICI Americas).

The above solutions are diluted to 2.5% by volume for application to the leaflets being treated, and the results are as follows:

|           | Mean score | Std dev. | Sig.* |
|-----------|------------|----------|-------|
| Water     | 4.70       | 0.57     | a     |
| $KHCO_3$  | 4.80       | 0.52     | a     |
| Control C | 4.60       | 0.82     | a     |
| Control D | 4.20       | 1.24     | ab    |
| Example 5 | 1.85       | 1.31     | c     |
| Example 6 | 1.20       | 0.95     | c     |
| Control E | 3.65       | 1.14     | b     |
| Example 7 | 1.65       | 1.27     | c     |

*Products with different letters are significantly different (p, 0.05) based on Duncan's multiple range test.

The results illustrate the advantage of an ethoxylated surfactant alcohol of the present invention over a food grade emulsifier described in the prior art.

The following comparative data are further illustrative of the superiority of an invention formulation in comparison with a prior art food grade emulsifier formulation for fungal control.

|               | Controls |      |      | Examples |      |      |
|---------------|----------|------|------|----------|------|------|
|               | F        | G    | H    | 8        | 9    | 10   |
| Span 20[1]    | 2.0      | 5.0  | 1.0  | 0.0      | 0.0  | 0.0  |
| Neodol 91-2.5[2] | 0.0   | 0.0  | 0.0  | 2.0      | 5.0  | 1.0  |
| $KHCO_3$      | 20.0     | 20.0 | 0.0  | 20.0     | 20.0 | 0.0  |
| $NaHCO_3$     | 0.0      | 0.0  | 10.0 | 0.0      | 0.0  | 10.0 |
| Water         | 78.0     | 75.0 | 89.0 | 78.0     | 75.0 | 89.0 |

[1]Span 20 is sorbitan monolaurate with an HLB of 8.6 (ICI Americas).
[2]Neodol 91-2.5 is a $C_9$-$C_{10}$ alcohol ethoxylated with an average of 2.5 moles of ethylene oxide, and has an HLB of 8.5 (Shell).

The above solutions are diluted to 2.5% by volume for application to the leaflets being treated, and the results are as follows:

|              | Mean score | Std dev. | Sig.* |
|--------------|------------|----------|-------|
| Water        | 4.90       | 0.31     | a     |
| Control F    | 3.70       | 1.26     | cd    |
| Control G    | 3.85       | 1.27     | bc    |
| Example 8    | 1.40       | 0.94     | e     |
| Example 9    | 1.10       | 0.91     | e     |
| Control H[1] | 4.40       | 0.68     | ab    |
| Example 10[1]| 3.15       | 1.23     | d     |

*Products with different letters are significantly different (p, 0.05) based on Duncan's multiple range test.
[1]Note Control H and Example 10 employ one half of the bicarbonate level used in Control F, Control G, Example 8 and Example 9, and therefore cannot be compared directly with the other formulations.

The comparative data confirm the advantages of invention surfactants over a food grade emulsifier of the prior art.

The following comparative data are further illustrative of the superiority of invention formulations in comparison with prior art food grade emulsifier formulations for fungal control.

|                  | Controls |      |      |      | Examples |      |
|------------------|----------|------|------|------|----------|------|
|                  | I        | J    | K    | L    | 11       | 12   |
| Span 80[1]       | 0.0      | 5.0  | 0.0  | 0.0  | 0.0      | 0.0  |
| Span 85[2]       | 0.0      | 0.0  | 5.0  | 0.0  | 0.0      | 0.0  |
| Glycosperse 0-20[3] | 0.0   | 0.0  | 0.0  | 5.0  | 0.0      | 0.0  |
| Renex 30[4]      | 0.0      | 0.0  | 0.0  | 0.0  | 5.0      | 0.0  |
| Atplus S-10[5]   | 0.0      | 0.0  | 0.0  | 0.0  | 0.0      | 5.0  |
| $KHCO_3$         | 20.0     | 20.0 | 0.0  | 20.0 | 20.0     | 0.0  |
| Water            | 75.0     | 75.0 | 75.0 | 75.0 | 75.0     | 75.0 |

[1]Span 80 is sorbitan mono-oleate with an HLB of 4.3 (ICI Americas).
[2]Span 85 is sorbitan trioleate with an HLB of 1.8 (ICI Americas).
[3]Glycosperse 0-20 is a 20 mole ethoxylated sorbitan mono-oleate with an HLB of 15.0 (Lonza).
[4]Renex 30 is an ethoxylated alcohol with an HLB of 14.5 (ICI Americas).
[5]Atplus is a 1:1 urea complex of polyethoxylated tridecyl alcohol with an HLB of 14.5 (ICI Americas).

The above solutions were diluted to 2.5% by volume for application to the leaflets being treated, and the results are as follows:

|            | Mean score | Std dev. | Sig.* |
|------------|------------|----------|-------|
| Water      | 4.65       | 0.49     | a     |
| $KHCO_3$   | 4.50       | 0.89     | a     |
| Control J  | 4.25       | 0.79     | a     |
| Control K  | 4.45       | 0.69     | a     |
| Control L  | 3.60       | 1.14     | b     |
| Example 11 | 2.50       | 0.89     | c     |
| Example 12 | 2.40       | 1.05     | c     |

*Products with different letters are significantly different (p, 0.05) based on Duncan's multiple range test.

The comparative data confirm that ethoxylated alcohol surfactants of the present invention outperform food grade emulsifiers, such as sorbitan mono-oleate, sorbitan trioleate and sorbitan mono-oleate ethoxylated with 20 moles of ethylene oxide. The HLB of sorbitan mono-oleate and sorbitan trioleate are below the lower limit of the invention surfactants, so that no corresponding ethoxylated alcohol can be compared. However, the ethoxylated alcohols in Examples 11–12 have an HLB similar to the ethoxylated sorbitan mono-oleate.

The following comparative data confirm the unexpected properties of invention fungicid. formulations for fungal control.

|  | Controls | | Examples | | | |
| --- | --- | --- | --- | --- | --- | --- |
|  | M | N | 13 | 14 | 15 | 16 |
| Neodol 25-9[1] | 0 | 0 | 1 | 1 | 0 | 0 |
| Triton N-101[2] | 0 | 0 | 0 | 0 | 1 | 1 |
| Tween 20 | 1 | 1 | 0 | 0 | 0 | 0 |
| KHCO$_3$ | 20 | 0 | 20 | 0 | 20 | 0 |
| NaHCO$_3$ | 0 | 10 | 0 | 10 | 0 | 10 |
| Water | 79 | 89 | 79 | 89 | 79 | 89 |

[1]Neodol 25-9 is a $C_{12}$–$C_{15}$ alcohol ethoxylated with an average of 9 moles of ethylene oxide, and has an HLB of 13.1 (Shell).
[2]Triton N-101 is an ethoxylated nonylphenol with an HLB of 13.4 (Union Carbide).

The above solutions were diluted to 2.5% by volume for application to the leaflets being treated, and the results are as follows:

|  | Mean score | Std dev. | Sig.* |
| --- | --- | --- | --- |
| Example 13 | 1.3 | 0.92 | c |
| Example 14 | 2.2 | 1.32 | c |
| Example 15 | 1.85 | 1.14 | c |
| Example 16 | 2.00 | 1.26 | c |
| Control M | 3.2 | 0.89 | b |
| Control N | 3.05 | 0.89 | b |
| Water | 4.95 | 0.22 | a |

*Products with different letters are significantly different (p, 0.05) based on Duncan's multiple range test.

The comparative data confirm the advantages of invention surfactants over a food grade emulsifier of the prior art.

The following comparative data demonstrate the effect of HLB of an ethoxylated surfactant on the performance of formulations for fungal control.

|  | 17 | 18 | 19 | 20 | 21 |
| --- | --- | --- | --- | --- | --- |
| Triton X-705[1] | 5.0 | 0.0 | 0.0 | 0.0 | 0.0 |
| Triton N-101 | 0.0 | 5.0 | 0.0 | 0.0 | 0.0 |
| Neodol 25-9 | 0.0 | 0.0 | 5.0 | 0.0 | 0.0 |
| Neodol 23-5 | 0.0 | 0.0 | 0.0 | 5.0 | 0.0 |
| Triton X-45[2] | 0.0 | 0.0 | 0.0 | 0.0 | 5.0 |
| KHCO$_3$ | 20.0 | 20.0 | 20.0 | 20.0 | 20.0 |
| Water | 79.9 | 79.8 | 79.5 | 79.0 | 78.0 |

[1]Triton X-705 is ethoxylated octylphenol with an HLB of 18.5 (Union Carbide).
[2]Triton X-45 is ethoxylated octylphenol with an HLB of 10.4 (Union Carbide).

The above solutions were diluted to 2.5% by volume for application to the leaflets being treated, and the results are as follows:

|  | HLB | Mean score | Std dev. | Sig.* |
| --- | --- | --- | --- | --- |
| F-17 | 18.7 | 3.55 | 1.05 | b |
| F-18 | 13.4 | 2.40 | 1.19 | c |
| F-19 | 13.1 | 2.60 | 1.50 | c |
| F-20 | 10.7 | 1.45 | 1.10 | d |
| F-21 | 10.4 | 1.25 | 1.16 | d |
| Water | N/A | 4.80 | 0.41 | a |

*Products with different letters are significantly different (p, 0.05) based on Duncan's multiple range test.

The comparative data show that performance generally increases with decreasing HLB of the surfactant used. Above an HLB of about 15, the performance is ineffective. The best performance is with an HLB between about 8–11.

The following comparative data demonstrate the effect of surfactant concentration on the efficacy of an invention formulation for fungal control.

|  | 22 | 23 | 24 | 25 | 26 |
| --- | --- | --- | --- | --- | --- |
| Neodol 91-2.5 | 0.1 | 0.2 | 0.5 | 1.0 | 2.0 |
| KHCO$_3$ | 20.0 | 20.0 | 20.0 | 20.0 | 20.0 |
| Water | 79.9 | 79.8 | 79.5 | 79.0 | 78.0 |

The above solutions were diluted to 2.5% by volume for application to the leaflets being treated, and the results are as follows:

|  | Mean score | Std dev. | Sig.* |
| --- | --- | --- | --- |
| F-22 | 3.45 | 0.99 | bc |
| F-23 | 3.60 | 1.19 | b |
| F-24 | 2.85 | 1.18 | cd |
| F-25 | 2.40 | 1.35 | d |
| F-26 | 0.80 | 1.20 | e |
| Water | 4.55 | 0.61 | a |

*Products with different letters are significantly different (p, 0.05) based on Duncan's multiple range test.

The comparative data show that performance of formulation becomes most effective above a concentration of about 0.01% in the diluted solution.

EXAMPLE III

This Example illustrates the preparation and application of a fungicide formulation in accordance with the present invention.

A blend of the following ingredients is prepared:

|  | Parts |
| --- | --- |
| sodium bicarbonate | 40.0 |
| potassium bicarbonate | 32.5 |
| Neodol 91-2.5 | 6.5 |
| kaolin | 20.0 |
| magnesium oxide | 1.0 |

The formulated concentrated powder is diluted with water by the dispersion of one part of the powder blend into 100 parts of water. The resulting solution is sprayed onto plant foliage where it forms an adherent coating on the foliage surfaces. The inclusion of xanthan gum (0.4 part) increases the quantity of fungicide adhering to leaves, thereby increasing the effectiveness against more resistant fungi.

The formulation is effective for fungus control with the following cultivated plants:

| Crop | Fungus |
| --- | --- |
| Grapevine | Uncinula necator |
| Grapevine | Plasmopara vitacola |
| Grapevine | Guignardia bidwellii |
| Grapevine | Botrytis cinerea |
| Rose | Sphaerotheca pannosa |
| Rose | Sphaerotheca humuli |
| Rose | Peronospora sparsa |
| Wheat | Erysiphe graminis |
| Wheat | Puccinia recondita |
| Apples | Podosphaera leucotricha |
| Alfalfa | Phoma medacaginis |

EXAMPLE IV

This Example illustrates the preparation and application of a fungicidal formulation in accordance with the present invention.

| | Parts |
|---|---|
| potassium bicarbonate | 50 |
| potassium carbonate | 5 |
| Triton X-45 | 6 |
| sodium carboxymethyl-cellulose[1] | 3 |
| water | 50 |

[1]Aldrich Chemical Co., CMC of 3000–6000 centipoises, intrinsic viscosity of 2% aqueous solution at 25° C.

The solid ingredients are blended, and the blend is suspended in water to form aqueous emulsion-paste.

The emulsion formulation is diluted with water to 0.5% by weight of bicarbonate ingredient. The diluted formulation is tested as a fungicide medium against plant foliage infected with powdery mildew. The fungicidal medium is 100% effective in mildew eradication, and prevents re-infection.

EXAMPLE V

This Example illustrates the preparation and application of dilute aqueous fungicidal formulations which are ready-to-use in agricultural applications.

A.

| | Parts |
|---|---|
| sodium bicarbonate | 0.5 |
| Neodol 1-9 | 0.025 |
| xanthan gum | 0.4 |
| water | 99.075 |

The ingredients are blended with the water in the listed order.

The dilute formulation is effective for control of powdery mildew and other fungal diseases when sprayed on plant foliage or fruit.

B.

The ingredients are blended with water in the listed order.

| | Parts |
|---|---|
| potassium bicarbonate | 1.0 |
| Neodol 91-6 | 0.1 |
| water | 98.9 |

The dilute solution is effective for control of powdery mildew when sprayed on plant foliage or fruit, The ingredients are blended in the listed order.

| | Parts |
|---|---|
| ammonium bicarbonate | 1.0 |
| Neodol 23-6.5 | 0.05 |
| polyvinylpyrrolidone | 0.10 |
| water | 98.85 |

The dilute formulation is especially effective for control of lettuce anthracnose, dollar spot and other leaf fungal diseases.

EXAMPLE VI

This Example illustrates the preparation and application of a fungicidal fertilizer composition for application to plant foliage and soil.

| | Parts |
|---|---|
| potassium bicarbonate | 10 |
| ammonium carbonate | 5 |
| Neodol 25-12 | 1 |
| carrageenan | 2 |
| dipotassium orthophosphate | 2 |
| water | 80 |

The ingredients are dispersed in the water to form a concentrated solution. The solution is diluted 1 part solution to 20 parts water before use.

A container of the solution is connected to agricultural sprayer equipment, and sprayed through a hollow cone spray nozzle at a pressure of 250 psi. The spray droplet size is 100–150 microns. A field of ornamental evergreen saplings is sprayed with the solution, and is effective for preventing fungal infection of the trees, and for promoting vigorous growth.

What is claimed is:

1. A method for controlling fungal disease in cultivated plants which comprises contacting the plant matter with a fungicidally effective amount of an aqueous formulation which has a content comprising (1) about 0.1–3 weight percent of a bicarbonate ingredient selected from the group consisting of alkali metal and ammonium bicarbonates; (2) about 0.01–0.5 weight percent of a surfactant ingredient selected from the group consisting of nonionic $C_{10}$–$C_{15}$ alcohols condensed with 8–15 moles of ethylene oxide having an HLB between about 8–15 and nonionic alkoxylated $C_6$–$C_{18}$ alkylphenols having an HLB between about 8–15; and (3) about 0.1–2 weight percent of an ingredient selected from the group consisting of phosphorus-containing fertilizer compounds; based on the formulation weight; wherein the ingredients have a formulated fertilizer-effective amount and ratio of nitrogen, phosphorus and potassium elements.

2. A method for controlling fungal disease in cultivated plants which comprises contacting the plant matter with a fungicidally effective amount of an aqueous formulation which has a content comprising (1) about 0.1–3 weight percent of a bicarbonate ingredient selected from the group consisting of alkali metal and ammonium bicarbonates; (2) about 0.01–0.5 weight percent of a surfactant ingredient selected from the group consisting of nonionic $C_{10}$–$C_{15}$ alcohols condensed with 8–15 moles of ethylene oxide having an HLB between about 8–15 and nonionic alkoxylated $C_6$–$C_{18}$ alkylphenols having an HLB between about 8–15; (3) about 0.01–0.4 weight percent of a water-soluble polymeric thickener-film forming ingredient; and (4) about 0.1–2 weight percent of an ingredient selected from the group consisting of phosphorus-containing fertilizer compounds; based on the formulation weight; wherein the ingredients have a formulated fertilizer-effective amount and ratio of nitrogen, phosphorus and potassium elements.

* * * * *